United States Patent
Shim et al.

(10) Patent No.: US 10,335,765 B2
(45) Date of Patent: Jul. 2, 2019

(54) COMPLEX OF CARBON STRUCTURE AND COVALENT ORGANIC FRAMEWORK, PREPARATION METHOD THEREFOR, AND USE THEREOF

(71) Applicant: KOREA INSTITUTE OF INDUSTRIAL TECHNOLOGY, Cheonan-si, Chungcheongnam-do (KR)

(72) Inventors: Jin Kie Shim, Seoul (KR); Chang Kee Lee, Cheonan-si (KR); Jong Tae Yoo, Bucheon-si (KR)

(73) Assignee: KOREA INSTITUTE OF INDUSTRIAL TECHNOLOGY, Cheonan-si, Chungcheongnam-Do (KR)

( * ) Notice: Subject to any disclaimer, the term of this patent is extended or adjusted under 35 U.S.C. 154(b) by 29 days.

(21) Appl. No.: 15/537,725

(22) PCT Filed: Dec. 18, 2015

(86) PCT No.: PCT/KR2015/013945
§ 371 (c)(1),
(2) Date: Aug. 21, 2017

(87) PCT Pub. No.: WO2016/099202
PCT Pub. Date: Jun. 23, 2016

(65) Prior Publication Data
US 2018/0272313 A1 Sep. 27, 2018

(30) Foreign Application Priority Data

Dec. 19, 2014 (KR) ........................ 10-2014-0184684

(51) Int. Cl.
*B01J 20/22* (2006.01)
*B01J 31/06* (2006.01)
*G01N 33/00* (2006.01)

(52) U.S. Cl.
CPC ............... *B01J 20/22* (2013.01); *B01J 31/06* (2013.01); *G01N 33/0036* (2013.01)

(58) Field of Classification Search
CPC ........ B01J 20/22; B01J 31/06; G01N 33/0036
(Continued)

(56) References Cited

U.S. PATENT DOCUMENTS 8,529,997 B2 * 9/2013 Heuft ................. H01L 51/0005
427/256
8,591,997 B2 * 11/2013 Heuft ..................... B82Y 10/00
427/384

(Continued)

FOREIGN PATENT DOCUMENTS

KR 1020090109090 A 10/2009
KR 1020100055350 A 5/2010

OTHER PUBLICATIONS

John W. Colson et al., "Oriented 2D Covalent Organic Framework Thin Films on Single-Layer Graphene." Scence, vol. 332, pp. 228-231 (Year: 2011).*

(Continued)

*Primary Examiner* — Patricia L. Hailey
(74) *Attorney, Agent, or Firm* — Cantor Colburn LLP

(57) ABSTRACT

The present invention relates to a complex comprising a covalent organic framework (COF) synthesized on the surface of a carbon structure, a preparation method therefor, and use thereof, and specifically to a complex of a carbon structure and a covalent organic framework, wherein the specific surface area or pore volume of the covalent organic framework synthesized on the surface of the carbon surface is larger than the specific surface area or the pore volume of the covalent organic framework prepared without the carbon structure; a preparation method therefor; and use thereof.

20 Claims, 7 Drawing Sheets

(58) Field of Classification Search
USPC .................. 502/172; 977/746, 748, 752
See application file for complete search history.

(56) References Cited

U.S. PATENT DOCUMENTS

| | | | | |
|---|---|---|---|---|
| 2011/0230678 | A1* | 9/2011 | Jung | C07F 5/025 564/11 |
| 2015/0266885 | A1* | 9/2015 | Banerjee | C07D 487/22 540/472 |

OTHER PUBLICATIONS

Adrien P. Cote, et al., "Porous, Crystalline, Covalent Organic Frameworks." Science, vol. 310, pp. 1166-1170 (Year: 2005).*

Biswal BP, et al., "Stabilization of graphene quantum dots (GQDs) by encapsulation inside zeolitic imidazolate framework nanocrystals for photoluminescence tuning",Nanoscale, 2013.

Elliot A. Roth, et al., "Nanoclay-Based Solid Sorbents for Co2 Capture", Energy Fuels 2013 27 (8) 4129-4136.

Eoghan P. Dillon, et al., "Synthesis, Characterization, and Carbon Dioxide Adsorption of Covalently Attached Polyethyleneimine-Functionalized Single-Wall Carbon Nanotubes", ACS Nano 2008, 2(1) 156-164.

Frederic Thebault, et al., "2,3,6,7,10,11-Hexahydroxytriphenylene tetrahydrate: a new form of an important starting material for supramolecular chemistry and covalent organic frameworks", Acta Cryst. 2011 C67, 143-145.

Maurisan A. Lino, et al., "Porous nanotubes and fullerenes based on covalent organic frameworks", Chemical Physics Letters 449 (2007) 171-174.

Wang Zhang, et al., "Microwave-assisted synthesis of highly fluorescent nanoparticles of a melamine-based porous covalent organic framework for trace-level detection of nitroaromatic explosives", Journal of Hazardous Materials 221-222 (2012) 147-154.

Weilong Wang, et al., "Development of a new clay supported polyethylenimine composite for CO2 capture", Applied Energy, vol. 113, 2014, 334-341.

* cited by examiner

COMPLEX OF CARBON STRUCTURE AND COVALENT ORGANIC FRAMEWORK, PREPARATION METHOD THEREFOR, AND USE THEREOF

TECHNICAL FIELD

The present invention relates to a complex of a carbon structure and a covalent organic framework, a preparation method therefor, and use thereof.

BACKGROUND ART

Porous materials have drawn attention in various application fields, such as gas storage and separation, sensors, and catalysts. Currently, development of new porous materials having easily controllable chemical affinities with high surface area is highly demanded. In this light, a covalent organic framework (COF) can be built by a covalent bond between organic molecular units, such as polyboronic acids and polythiol compounds. Further, metal organic frameworks (MOFs) are emerging as one of the most promising materials as a gas adsorbent because the pore sizes and chemical affinities are easily-controllable by modifying the metals and linkers. Additionally, the COF is capable of forming various complexes, and thus has been studied for new applications beyond a gas adsorbent.

Meanwhile, carbon nanotube (CNT) and graphene combine their remarkable electrical, chemical, thermal, optical, and mechanical properties with a huge surface area, and thus have been considered as hybrid materials in a broad range of applications, such as polymer reinforcing agents, electronic devices, and biological applications. These potential applications, however, are often limited due to the strong van der Waals interactions of a π-donor surface, which result in poor dispersion in CNTs and graphene.

DETAILED DESCRIPTION OF THE INVENTION

Technical Problem

An object of the present invention is to provide a complex of a carbon structure and a covalent organic framework synthesized on the surface of a carbon structure having increased specific surface area or pore volume, a preparation method therefor, and use thereof.

Technical Solution

A first embodiment of the present invention provides a complex comprising a covalent organic framework (COF) synthesized on the surface of a carbon structure.

A second embodiment of the present invention provides a preparation method for the complex of the first embodiment, comprising adding the carbon structure and reactants used for synthesizing covalent organic framework to a solvent, followed by ultrasonic treatment (Step 1).

A third embodiment of the present invention provides a composition of adsorbing, storing, separating, or concentrating gases comprising the complex of the first embodiment.

A fourth embodiment of the present invention provides a gas sensor comprising the complex of the first embodiment.

Hereinafter, the present invention will be described in more detail.

A covalent organic framework (COF) is an extended organic structure which is formed by organic building units covalently connected, and can be formed mainly by H, B, C, N, and O, which are light atoms. The covalent organic framework has not only a rigid porous (micro- and mezzo-porous) structure, but also excellent thermal stability and low density. Further, the COF has larger specific surface area than that of commonly known materials such as zeolite and porous silicates.

The synthesis of the covalent organic framework starts from the formation of covalent bonds of building units. Various covalent organic frameworks can be formed by various rigid organic building units in different structural arrangements. Further, a strong covalent bond can be formed through various organic synthesis reactions, and thereby a COF material having a well-defined 2D or 3D crystal structure can be provided. Assembly of building units in the metal organic framework (MOF) can be self-adjusted through a coordinate bond, whereas structural regularity of the COF may be difficult to be controlled through a strong covalent bond. For synthesis applicable to building of the COF structure, various reversible reactions like the reaction formulae below may be desirable.

A

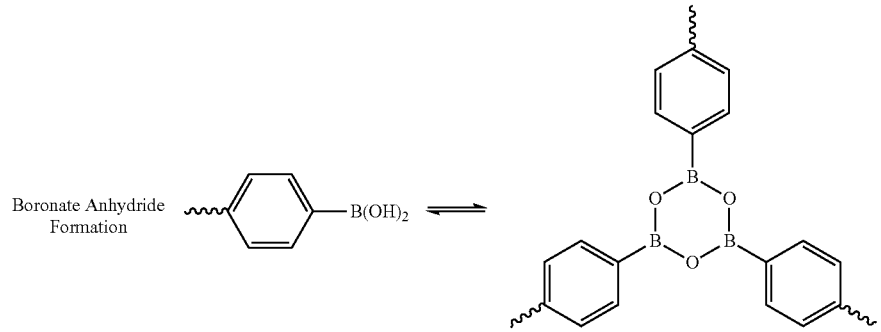

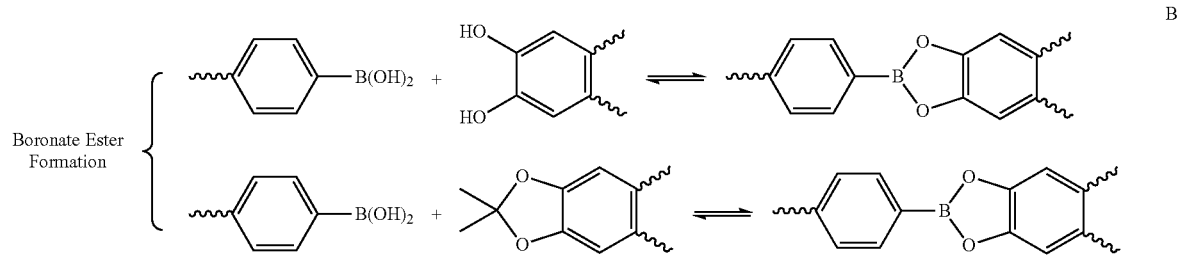
Boronate Ester Formation
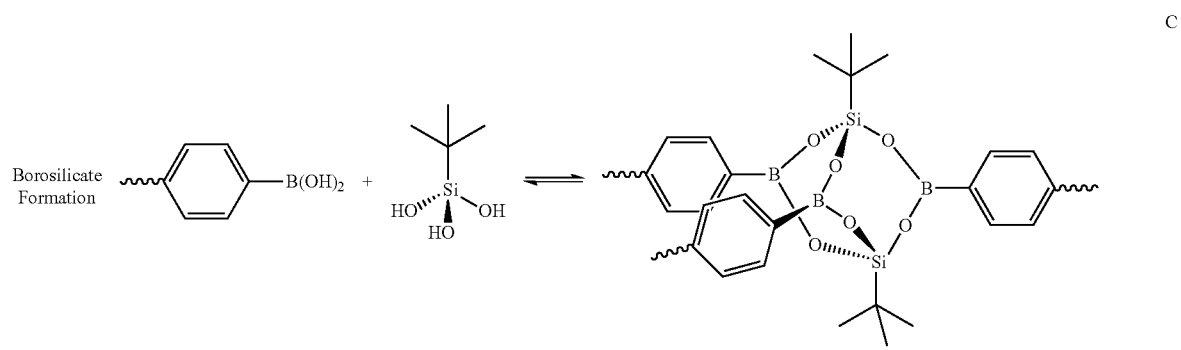
Borosilicate Formation
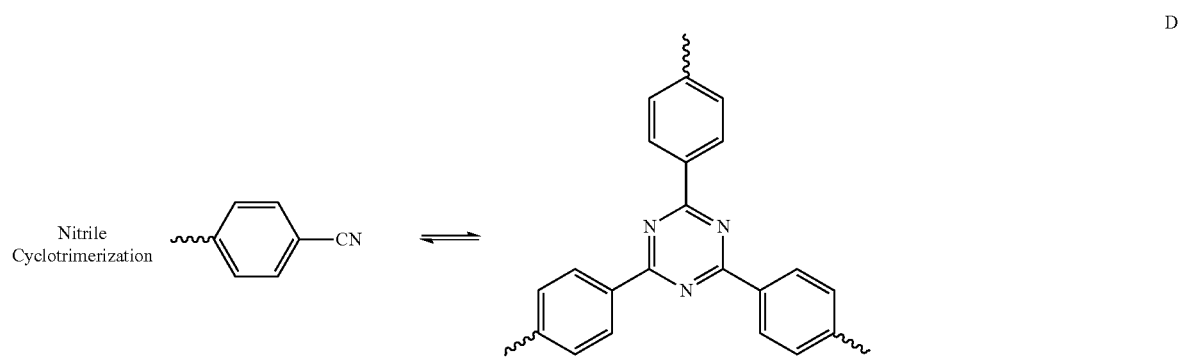
Nitrile Cyclotrimerization
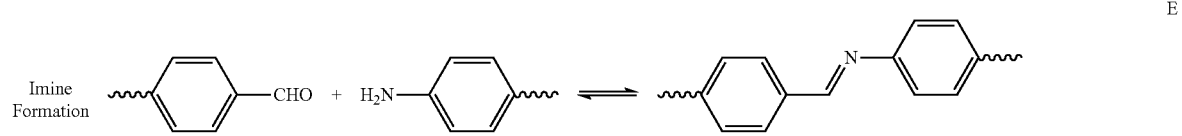
Imine Formation
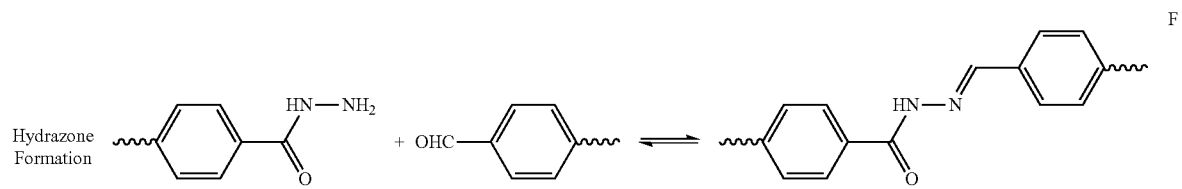
Hydrazone Formation Further, for building units of the COF through the above synthesis reactions, that is, reactants of the covalent organic framework, various compounds shown below can be used.
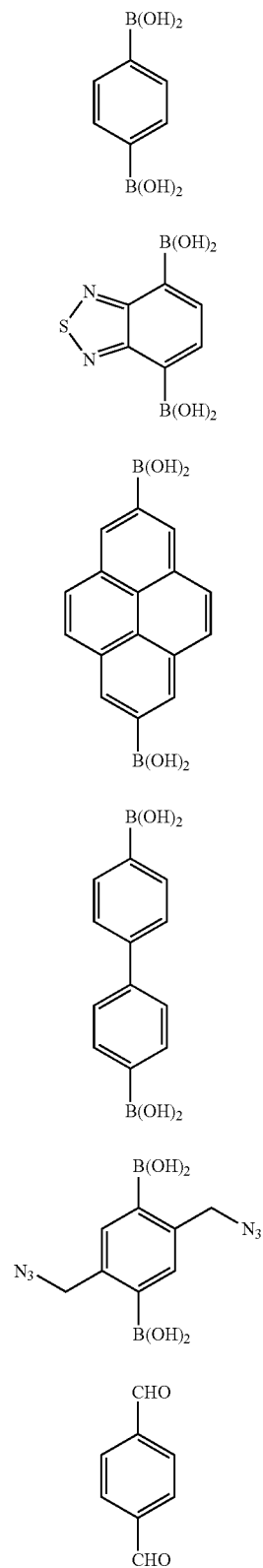
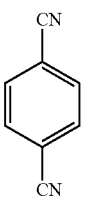
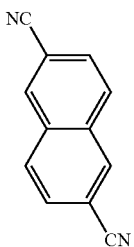
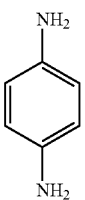
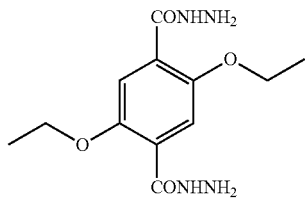
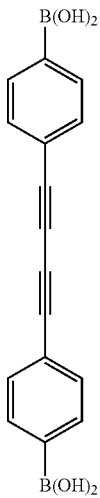

-continued
12
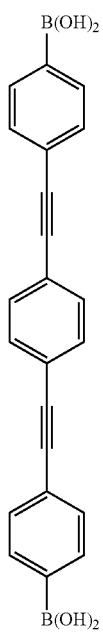
13
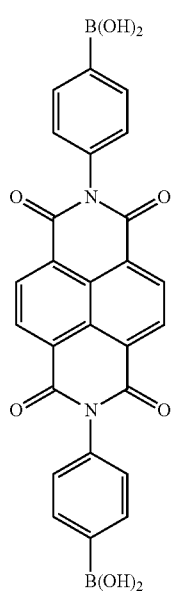
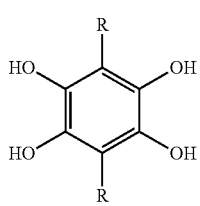
R = H      14a
R = CH₃    14b
R = CH₂CH₃ 14c
R = CH₂CH₂CH₃ 14d
-continued
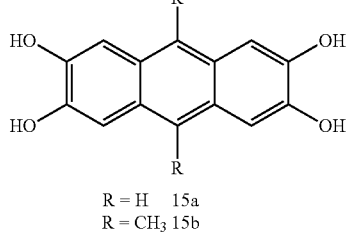
R = H     15a
R = CH₃   15b
16
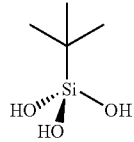
17
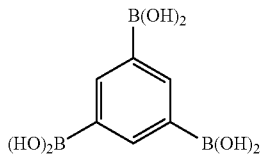
18
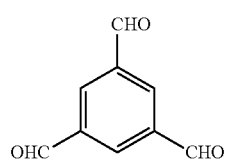
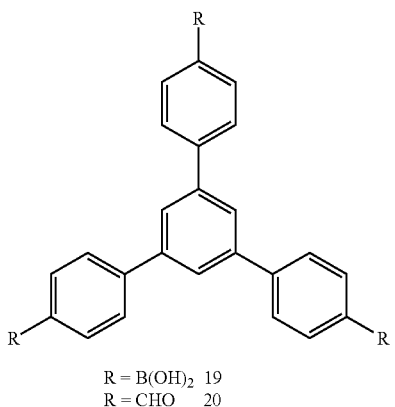
R = B(OH)₂  19
R = CHO     20
21
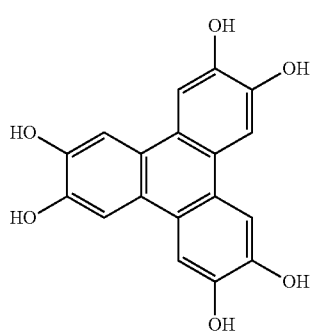

-continued
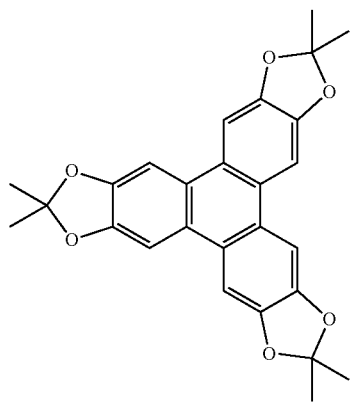
22
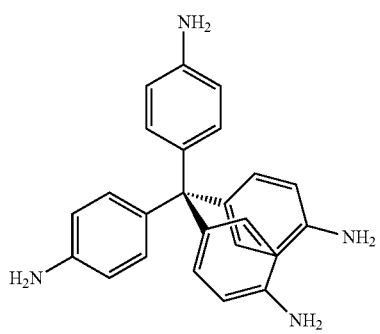
23
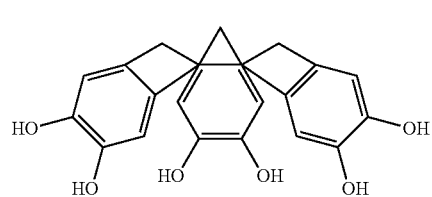
24
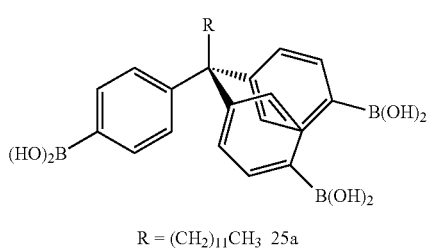
R = (CH₂)₁₁CH₃  25a
R = allyl  25b
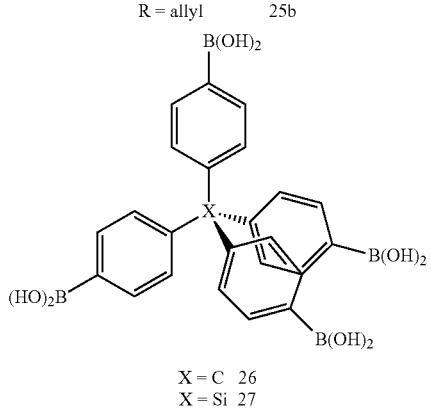
X = C  26
X = Si  27
-continued
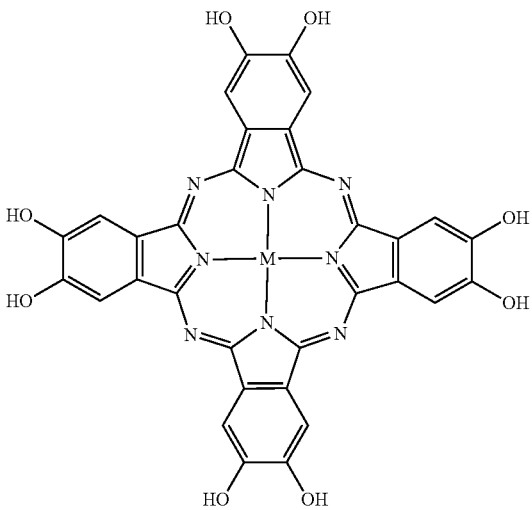
M = Ni (28a); Zn (28b)
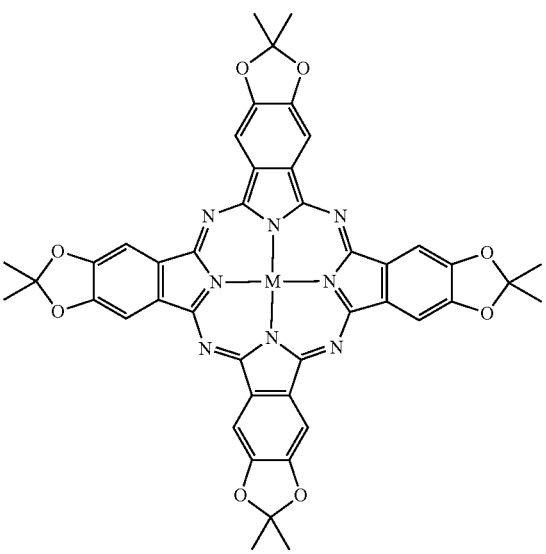
M = 2H (29a); Ni (29b)

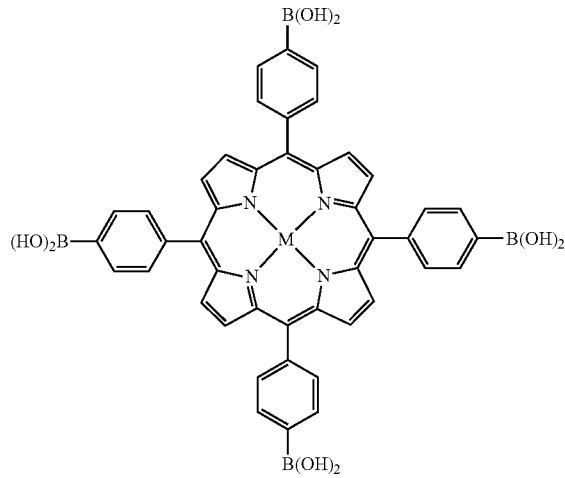

M = 2H (30a); Zn (30b); Cu (30c)

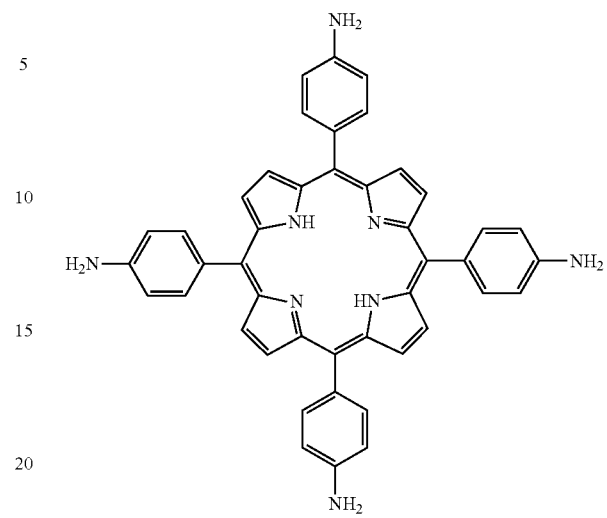

31

Examples of COF formed through various organic synthesis reactions of the above organic building units may be the COFs shown in Table 1 below. Table 1 also shows structural information of each COF.

TABLE 1

| Type | Material | Building unit(s)[a] | Synthetic reaction[b] | Space group | Pore size[c] (Å) | BET surface area ($m^2$ $g^{-1}$) | Ref. |
|---|---|---|---|---|---|---|---|
| Boron-containing | COF-1 | 1 | A | P6$_3$/mmc | 7 | 711 | 9 |
| | COF-102 | 26 | A | I$_{43}$d | 12 | 3472 | 41 |
| | COF-103 | 27 | A | I$_{43}$d | 12 | 4210 | 41 |
| | PPy-COF | 3 | A | P6/mmm | 17 | 923 | 89 |
| | COF-102-C$_{12}$ | 25a + 26 | A | I$_{43}$d | — | >2000 | 91 |
| | COF-102-allyl | 25b + 26 | A | I$_{43}$d | — | — | 91 |
| | COF-5 | 1 + 21/22 | B | P6/mmm | 27 | 1590 | 9 |
| | COF-105 | 26 + 21 | B | I$_{43}$d | 21 | — | 41 |
| | COF-108 | 27 + 21 | B | P$_{43}$d | 19, 31 | — | 41 |
| | COF-6 | 17 + 21 | B | P6/mmm | 9 | 750 | 92 |
| | COF-8 | 19 + 21 | B | P6/mmm | 16 | 1350 | 92 |
| | COF-10 | 4 + 21/12 | B | P6/mmm | 32 | 1760 | 92 |
| | COF-11Å | 17 + 14d | B | P6/mmm | 11 | 105 | 49 |
| | COF-14Å | 17 + 14c | B | P6/mmm | 14 | 805 | 49 |
| | COF-16 | 17 + 14b | B | P6/mmm | 16 | 753 | 49 |
| | COF-18Å | 17 + 14a | B | P6/mmm | 18 | 1263 | 49 |
| | TP-COF | 3 + 21 | B | P6/mmm | 32 | 868 | 51 |
| | Pc-PBBA COF | 1 + 29a | B | P4/mmm | 20 | 450 | 48 |
| | NiPc-PBBA COF | 1 + 28a/29b | B | P4/mmm | 23 | 776 | 73 and 74 |
| | 2D-NiPc-BTDA COF | 2 + 28a | B | P4 | 22 | 877 | 93 |
| | NiPc COF | 1 + 28a | B | P4/mmm | 19 | 624 | 94 |
| | BTP-COF | 19 + 15b | B | P6/mmm | 40 | 2000 | 95 |
| | HHTP-DPB COF | 11 + 21 | B | P6/mmm | 47 | 930 | 90 |
| | x%N$_3$-COF-5 (x = 5, 25, 50, 75, 100) | 5 + 21 | B | P6/m | 18-29[d] | 1421-2160 | 65 |
| | 100%N$_3$-NiPc-COF | 5 + 28a | B | P4/mmm | 18[d] | 675 | 65 |
| | COF-66 | 30a + 15a | B | P4/mmm | 23 | 360 | 96 |
| | ZnPc-Py COF | 3 + 28b | B | P4/mmm | 27 | 420 | 50 |
| | ZnPc-DPB COF | 11 + 28b | B | P4/mmm | 34 | 485 | 50 |
| | ZnPc-NDI COF | 13 + 28b | B | P4/mmm | 40 | 490 | 50 |
| | ZnPc-PPE COF | 12 + 28b | B | P4/mmm | 44 | 440 | 50 |
| | CTC-COF | 1 + 24 | B | P3m1 | 23 | 1710 | 97 |
| | H$_2$P-COF | 30a + 14a | B | P1 | 25 | 1894 | 149 |
| | ZnP-COF | 30b + 14a | B | P1 | 25 | 1713 | 72 and 149 |
| | CuP-COF | 30c + 14a | B | P1 | 25 | 1724 | 149 |
| | COF-202 | 16 + 26 | C | I$_{43}$d | 11 | 2690 | 98 |
| Triazine-based | CTF-1 | 7 | D | P6/mmm | 12 | 791 | 56 |
| | CTF-2 | 8 | D | P6$_3$/mmc | 20 | 90 | 83 |
| Imine-based | COF-300 | 23 + 6 | E | I$_4$1a | 8 | 1360 | 57 |
| | COF-LZU1 | 9 + 18 | E | P6/m | 18 | 410 | 66 |
| | COF-366 | 31 + 6 | E | P4/m | 20 | 735 | 96 |
| | COF-42 | 10 + 18 | F | P6/m | 28 | 710 | 58 |
| | COF-43 | 10 + 20 | F | P6/m | 35 | 620 | 58 |

As shown in Table 1, the covalent organic frameworks are specifically COF-1, COF-102, COF-103, PPy-COF, COF-102-C$_{12}$, COF-102-allyl, COF-5, COF-105, COF-108, COF-6, COF-8, COF-10, COF-11 Å, COF-14 Å, COF-16 Å, COF-18 Å, TP-COF, Pc-PBBA COF, NiPc-PBBA COF, 2D-NiPc-BTDA COF, NiPc COF, BTP-COF, HHTP-DPB COF, x % N$_3$-COF-5(x=5, 25, 50, 75, or 100), 100% N$_3$-NiPc-COF, COF-66, ZnPc-Py COF, ZnPc-DPB COF, ZnPc-NDI COF, ZnPc-PPE COF, CTC-COF, H2P-COF, ZnP-COF, CuP-COF, COF-202, CTF-1, CTF-2, COF-300, COF-LZU1, COF-366, COF-42, COF-43, etc. Further, COF-320, COF-102-Li, COF-103-Li, COF-102-Na, COF-103-Na, COF-301-PdCl$_2$, COF-103-Eth-trans, COF-102-Ant, etc., are known as covalent organic frameworks.

A successful embodiment of a COF material through such organic building units can provide a covalent framework which can be functionalized as a lightweight material optimized for gas storage, photonics, and catalytic application.

Specifically, the covalent organic frameworks can be used as materials for adsorbing, storing, separating, and/or concentrating gases such as hydrogen, methane, and/or CO$_2$. The covalent organic frameworks can be categorized into the following three groups according to their structural dimension and size of pores. Group 1 is 2D frameworks having small pores of 1D (10 Å or below), such as COF-1 and COF-6 (9 Å, respectively). Group 2 is 2D frameworks having big pores of 1D (15 Å or above, and preferably 15 Å to 40 Å), such as COF-5 (27 Å), COF-8 (16 Å), and COF-10 (32 Å). Group 3 is 3D frameworks having medium-sized pores of 3D (10 Å to 15 Å), such as COF-102 and COF-103 (12 Å, respectively). In terms of performance in adsorbing, storing, separating, and/or concentrating gases, group 3 can exceed groups 1 and 2. However, in terms of synthesis, group 3 may not be easy compared to groups 1 and 2. Specifically, with regard to gas adsorption uptakes by COF-102 at 35 bar, hydrogen uptake is 72 mg g$^{-1}$ at 77K, methane uptake 187 mg g$^{-1}$ at 298K, and carbon dioxide uptake 1180 mg g$^{-1}$ at 298K. Such gas adsorption uptakes by COF-102 are similar with those by COF-103, but are higher than those by COF-1, COF-5, COF-6, COF-8, and COF-10. Hydrogen uptakes at 77K are 15 mg for COF-1, 36 mg g$^{-1}$ for COF-5, 23 mg g$^{-1}$ for COF-6, 35 mg g$^{-1}$ for COF-8, and 39 mg for COF-10. Methane uptakes at 298K are 40 mg g$^{-1}$ for COF-1, 89 mg g$^{-1}$ for COF-5, 65 mg g$^{-1}$ for COF-6, 87 mg g$^{-1}$ for COF-8, and 80 mg g$^{-1}$ for COF-10. Carbon dioxide uptakes at 298K are 210 mg g$^{-1}$ for COF-1, 779 mg g$^{-1}$ for COF-5, 298 mg g$^{-1}$ for COF-6, 598 mg g$^{-1}$ for COF-8, and 759 mg g$^{-1}$ for COF-10. As shown above, COF-5 among the COFs of groups 1 and 2 exhibits excellent gas adsorption uptakes in general.

In addition, the highest H2 uptakes at 77K are 10.0 wt % at 80 bar for COF-105 and 10.0 wt % at 100 bar for COF-108, as the COF are linked to high surface area and free volume of COF. Further, as a strategy to improve the H$_2$ uptake, there is a method of modifying COF for higher interaction with H$_2$. Specifically, the COF may be metalized into alkali metals, such as Li, Na, K, etc., to form a complex, and thereby increasing H$_2$ adsorption uptakes. Such complexes are COF-102-Li, COF-103-Li, COF-102-Na, COF-103-Na, etc. Further, COF-301-PdCl$_2$, etc., may be used as a COF modified to enhance the H$_2$ uptake. An excellent COF in terms of total volume of CH$_4$ per unit volume COF adsorbent is COF-1, which can store 195 v/v of methane at 298 K and 30 bar. Superior COFs on a delivery amount basis are COF-102 and COF-103 with values of 230 v and 234 v (STP: 298 K, 1.01 bar)/v, respectively, and other superior COFs are COF-103-Eth-trans, COF-102-Ant, etc.

Further, the covalent organic frameworks can be applied in the field of catalysts, and their excellent optical and electrical properties enable their application to the field of electric and electronic devices. Specifically, Pd/COF-LZU1, which is a metalized COF, may be used as a catalyst in the Suzuki-Miyaura coupling reaction. Further, a highly ordered π-conjugation TP-COF, consisting of pyrene and triphenylene functional groups alternately linked in a mesoporous hexagonal skeleton, is highly luminescent, harvests photons of a wide range of wavelength, and allows energy transfer and migration. TP-COF is also electrically conductive and capable of repetitive on-off current switching at room temperature.

For synthesis of covalent organic frameworks, solvothermal, microwave irradiation, and sonochemical methods, etc., may be used. The solvothermal method synthesizes a COF by heating (at a temperature of 80° C. to 120° C.) in a vacuum-sealed container where the pressure may influence reaction yields. Further, types of solvents may influence solubility and crystallization of COF reactants. The covalent organic frameworks are mostly synthesized by the solvothermal method. The speed of crystallization through the solvothermal method is slow, taking several days of reaction period. Accordingly, it is demanded to develop a COF synthesis method which enables more rapid crystallization. Recently, rapid COF synthesis methods which facilitate the synthesis reaction by adding microwaves or ultrasonic waves have been reported. For example, a sonochemical synthesis method is a method which accelerates a rate of crystallization, that is, a rate of COF synthesis, in a sonochemical synthesis reaction by formation and collapse of bubbles in a solution, which is called acoustic cavitation. Acoustic cavitation produces an intense local temperature (>5000 K) and pressure (>1000 bar), and thereby providing extremely fast heating and cooling speeds.

The present invention has found that the pore volume of the covalent organic framework synthesized on the surface of the carbon structure to prepare a complex is larger than that of the covalent organic framework prepared without the carbon structure, which is the basis of the present invention.

As previously mentioned, one embodiment of the present invention can provide a complex prepared by synthesizing a covalent organic framework (COF) on the surface of a carbon structure. Specifically, the present invention can provide a complex prepared by in situ synthesis of COF reactants on a carbon structure. The carbon structure is a versatile structure composed of carbon in various forms, and can be used in the various technical fields because of its various excellent properties.

In the present invention, the carbon structure may be in a micro- to nano-size, and preferably in a nano-size. The carbon nanostructure may refer to a structure in a size range of several nanometers (nm) to hundreds of nanometers.

In the present invention, the carbon structure may be at least one type selected from the group consisting of a carbon nanotube, a carbon nanowire, graphene, graphene oxide, and carbon black, but is not limited thereto.

In the present invention, particularly preferably, a carbon nanotube (CNT) may be used as the carbon structure. The carbon nanotube is an allotrope of carbon having a cylindrical tube structure, and may be divided into single-walled (SW) nanotubes composed of a single tube, double-walled (DW) nanotubes composed of two tubes stacked on top of one another, multi-walled (MW) nanotubes composed of at least three tubes, etc. The single-walled nanotubes have a low production yield and a complicated purification process, and thus, the multi-walled nanotubes may be mainly used.

The carbon nanotubes have high surface area of 50 m²/g to 1315 m²/g, leading to an excellent capability to store gas. Further, they have a specific nano space within the CNT bundle, such as channels between grids and external groove, thereby displaying strong interaction with aromatic molecules and gas molecules such as Ar, Ne, He, $CF_4$, $H_2$, $N_2$, $O_2$, and $C_nH_{2n+2}$, and molecular selectivity. However, somewhat low gas selectivity and storage capacity caused by the π-donor surface of CNT result in a limitation on the application to gas sensors and gas separation. The complex of the present invention has the i-donor surface on the CNT surface, coated with the covalent organic framework, and thus improving gas adsorption capability and gas selectivity compared with using the CNT solely.

Additionally, as previously mentioned, carbon nanowire, graphene, graphene oxide, carbon black, etc., can be effectively used as the carbon structure. A carbon nanowire is a huge one-dimensional structure consisting of carbon with a length of several to dozens of μm, a diameter around 100 nm, and an extreme aspect ratio. Graphene is a conductive material consisting of a single-atom-thick hexagonal lattice of carbon atoms. Graphene is attracting a lot of attention as a material whose application field is indefinitely versatile because of its extraordinary flexibility and thermal and electric conductivity. The crystalline structure of graphene is in the form where bonds in a hexagonal lattice are stretching out toward a two-dimensional direction by an atomic structure in which three bonds are linked to one apex ($sp^2$ bond). Consequently, graphene has a two-dimensional crystalline form in a widespread honeycomb lattice, and forms a hexagonal cavity. Accordingly, graphene may exist in a single-atom-thick thin film and in a stable molecular structure, and may be very transparent. Graphene oxide, as an oxidized form of graphene, may have a two-dimensional form, and has properties, such as excellent water solubility, amphipathy, easy surface functionalization, surface-enhanced Raman scattering (SERS), and fluorescence quenching. Carbon black is an agglomerate of soot produced by incomplete combustion of hydrocarbons and the like, such as natural gas, tar, oil, etc., or an agglomerate of crystallites in a carbon hexagonal mesh structure obtained by formation of multi-ring aromatics after processes including dehydrocondensation followed by formation of six-carbon rings by thermal decomposition.

As previously mentioned, the present invention confirmed that a complex can be prepared by synthesizing a COF on the surface of a carbon structure, and that the specific surface area or pore volume of the prepared COF synthesized on the surface of the carbon structure is larger than that of the COF prepared without the carbon structure under the same synthesis conditions. Specifically, an Example of the present invention confirmed that an improved $CO_2$ uptake was observed in the CNT@COF-5 than COF-5 as well as the pristine CNT (FIG. 7), which seems attributed to synthesis into a small microcrystalline agglomerate because the high curvature of the CNT surfaces hinders the formation of large microcrystallites by COF-5.

Accordingly, the complex of the present invention including the covalent organic framework with the increased specific surface area or pore sizes has the previously-mentioned features, which are capabilities for gas adsorption, storage, separation, and/or concentration, and thus can be effectively employed as agents for adsorbing, storing, separating, and/or concentrating gases.

Further, the complex of the present invention is applicable to a catalyst because of carrying capacity of a catalytic material which the covalent organic framework has, and to a light-emitting material or a semiconductor because of COF's optical and electrical properties. In addition, the complex of the present invention is widely applicable in an extensive range where the COF is applicable.

In the present invention, reactants of the covalent organic framework may preferably be aromatic compounds capable of π-π stacking. Aromatic compounds, such as benzene, pyrene, anthracene, triphenylene, and porphyrin derivatives, which are used as building blocks for the COFs, have strong adhesiveness to a carbon structure such as CNTs due to the strong π-π stacking. Accordingly, through dispersion by stirring and/or ultrasonic treatment, the aromatic compounds can effectively adsorb to the surfaces of the carbon structure and be solvated, and thus can be used as solubilizers of the carbon structure. Additionally, the π-π interaction between the reactants and the surface of the carbon structure plays a role of controlling the COF formation only onto the surface of the carbon structure in order to form a well-controlled complex on the surface of the carbon structure.

In the present invention, using COF-5 among others as a COF may be preferred because of its $CO_2$ adsorbing property and simple synthesis methods. COF-5 can be synthesized by a sonochemical method as well as a solvothermal reaction and microwave irradiation. Accordingly, by using the COF-5 as the COF, the present invention simultaneously performs molecular adsorption and synthesis of the COF-5 reactants on the surfaces of CNT and graphene by the ultrasonic treatment, and thereby preparing the complex of the present invention in a more simple synthesis method.

As illustrated in FIG. 1, an Example of the present invention confirmed that COF-5, which is one of the COFs, can be synthesized on the surfaces of the CNT (CNT@COF-5) and the graphene (graphene@COF-5), which are carbon structures, by in situ sonochemical reactions during the dispersion process.

Further, one embodiment of the present invention can provide a preparation method of the complex comprising the step below.

the carbon structure and reactants used for synthesizing covalent organic framework are added to a solvent, followed by ultrasonic treatment (Step 1).

According to the preparation method of the complex of the present invention, the reactants used for synthesizing the covalent organic framework are adsorbed on the surface of the carbon structure by the ultrasonic treatment in Step 1, and the covalent organic framework can be formed by a sonochemical reaction. In other words, the preparation method of the complex of the present invention enables simultaneous performances of adsorption of the reactants onto the surface of the carbon structure by dispersion of reactants forming the COF by a single process of ultrasonic treatment, and synthesis of the COF by a sonochemical reaction. In this light, such relatively simple process of in situ synthesis of COF on the surface of the carbon structure is advantageous in preparing a complex. Specifically, the present invention confirmed the COF-5, which is one of the COFs, CNT, and graphene can be synthesized through sonochemical reactions by ultrasonic treatment after dispersion thereof (Example 1). That is, adsorption and synthesis reactions of the reactants forming the COF-5 can be simultaneously performed on the surfaces of CNT and graphene.

In the present invention, a concentration of the carbon structure may be 0.2 mg/mL to 2 mg/mL. If the concentration of the carbon structure is below 0.2 mg/mL, production yield of the complex is low, and thus bearing inefficiency, and if the concentration is above 2 mg/mL, the carbon structures are likely to cohere.

In the present invention, the reactants to form the COF may be various compounds which are known to form COFs in the art, and preferably aromatic compounds capable of π-π stacking with the surfaces of the carbon structures as mentioned previously. More preferably, the aromatic compounds may be the same capable of forming COFs by sonochemical synthesis. Specifically, the reactants to form COFs in an Example of the present invention are benzene-1,4-diboronic acid (BDBA), 2,3,6,7,10,11-hexahydroxytriphenylene (HHTP), or a mixture thereof.

In the present invention, a concentration of the reactants to form the COFs may be 10 mg/mL to 60 mg/mL. The formation of COFs may be difficult if the concentration of the reactant which forms the COF is below 10 mg/mL, and may be inefficient if the concentration is above 60 mg/mL.

In the present invention, the solvent may be mesitylene, 1,4-dioxane, or a mixture thereof, but is not limited thereto.

An ultrasonic wave may be defined as an inaudible frequency to humans, that is, a frequency of 16 kHz or higher. Ultrasonic wave in actual use has three regions having different frequency scopes, which may be high frequencies or diagnostic ultrasound (1 MHz to 10 MHz), low frequencies (20 kHz to 100 kHz), and middle frequencies (100 kHz to 1000 kHz). Ultrasonic wave used to facilitate a chemical reaction by using high temperature and pressure produced by formation, growth, and disintegration may mainly be low or middle frequencies, and preferably the middle frequency region. The ultrasonic wave used in (step 1) of the present invention may be preferably 20 kHz to 1000 kHz, and more preferably 50 kHz to 200 kHz.

The ultrasonic treatment of the present invention may preferably be conducted at an output power of 50 W to 500 W for 30 minutes to 6 hours. If the output power is below 50 W, the dispersion and sonochemical reactions by the ultrasonic treatment may not sufficiently occur. If the output power is above 500 W, the reactions could be inefficient. Further, if duration of the ultrasonic treatment is less than 30 minutes, the ultrasonic treatment may not sufficiently occur, and if it exceeds 6 hours, the treatment could be inefficient.

Preferably, after (step 1) of the present invention, (step 2) for collecting the resultants of (step 1) and washing may be further included.

In the present invention, (step 2) could be conducted by washing after removing the supernatant of centrifugation of the reactants of (step 1).

Additionally, the present invention can provide composition of adsorbing, storing, separating, or concentrating gases comprising the complex containing a covalent organic framework (COF) synthesized on the surface of a carbon structure.

In the present invention, the gas may be at least one gas selected from the group consisting of $CO_2$, Ar, Ne, He, $CF_4$, $H_2$, $N_2$, $O_2$, and $C_nH_{2n+2}$ (wherein n is an integer of 1 to 4), but is not limited thereto.

The complex of the present invention is capable of having gas adsorption capacity improved compared with that of a sole material of carbon structure or COF, and thus may be efficiently used for adsorbing, storing, separating, or concentrating gases (FIG. 7).

Further, the complex in the composition of the present invention for adsorbing, storing, separating, or concentrating gases can be functionalized as a catalyst as well as agents for adsorbing, storing, separating, or concentrating gases. That is, the complex in the composition of the present invention for adsorbing, storing, separating, or concentrating gases can be used as a catalyst.

In the present invention, the COF may be modified into metals, such as Pd, so that the complex can be used as a catalyst.

In the present invention, the complex can be used as a gas sensor.

The term "gas sensor" of the present invention may refer to a device which detects a gas having a specific ingredient in the air, and transfers appropriate electric signals depending on the gas concentration.

As mentioned previously, a successful embodiment of the COF by organic building units can provide a COF which can be functionalized as a light material optimized for gas storage. Further, carbon nanotubes, carbon nanowires, graphenes, oxide graphenes, carbon black, etc., which are applicable as carbon structures, have high surface area, and thus an excellent gas storage capacity. This combination of COFs and carbon structures enables gas storage capacity superior to sole use thereof. In particular, carbon nanotubes make strong interactions with aromatic and gas molecules, such as Ar, Ne, He, $CF_4$, $H_2$, $N_2$, $O_2$, and $C_nH_{2n+2}$, increases molecular selectivity, and thus is advantageous in the application as a gas sensor. Accordingly, the complex of the present invention is applicable as a physicochemical molecular gas sensor by using such properties.

Specifically, the gas sensor can be used to detect a gas selected from the group consisting of $CO_2$, Ar, Ne, He, $CF_4$, $H_2$, $N_2$, $O_2$, and $C_nH_{2n+2}$ (wherein n is an integer of 1 to 4), but is not limited thereto as long as the gas can be detected by the COF or carbon structure.

Further, the present invention can provide a sensor chip comprising the sensor. Preferably, the sensor chip may be in the form of a film.

Advantageous Effects

The present invention provides a complex prepared by synthesizing the covalent organic framework on the surface of the carbon structure, wherein the complex has the specific surface area or pore volume of the covalent organic framework synthesized which is larger than the specific surface area or the pore volume of the covalent organic framework prepared without the carbon structure, and thus a highly improved feature of gas adsorption.

PREFERRED EMBODIMENT OF THE INVENTION

Figure 1:
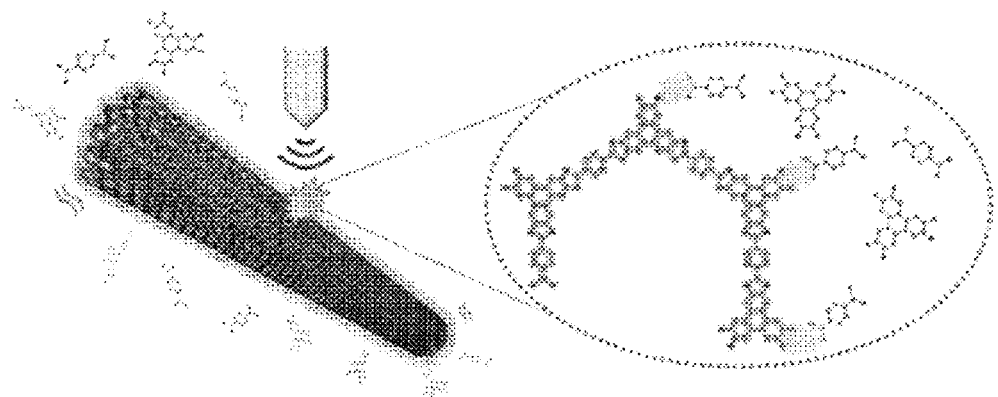
FIG. 1 schematically illustrates synthesis of CNT@COF-5, which is a complex of the present invention.

Hereinafter, the present invention will be described in more detail with reference to Examples. However, these Examples are for illustrative purposes only, and the invention is not intended to be limited by these Examples.

Example 1: Preparation of a Complex Through COF-5 Synthesis on the Surface of CNT or Graphene Materials Multi-walled nanotubes (MWNT) ($C_{tube}$ 120, metal oxides<3 wt %, average diameter: at most 20 nm, length: 1 μm to 25 μm, CNT Co., Ltd) and graphene (3 nm graphene nanopowder, grade AO-1, Graphene Supermarket) were used as provided. Benzene-1,4-diboronic acid (95%), acetone (99.9%), and 1,4-dioxane (99.8%) were purchased from the Sigma-Aldrich Corporation, and 2,3,6,7,10,11-hexahydroxytriphenylene (95%) (Tokyo Chemical Industry Co., Ltd.) and mesitylene (98%) (Kanto Chemical Co., Inc.) were used as provided.

Measurement Method

A measurement method using a field emission scanning electron microscope (FE-SEM) was performed using SU-8020 (Hitachi, Tokyo, Japan) at 1 kV, and Fourier transform infrared (FT-IR) spectrum was measured with Varian 660-IR (Varian Medical Systems, Inc., California, USA). The X-ray diffraction (XRD) measurements in the range of 2.5<2θ <20° were performed on a SmartLab (Rigaku, Tokyo, Japan) at 40 kV and 30 mA (CuK radiation, λ=0.154 nm) and the morphology of the composite was analyzed with atomic-force microscopy (AFM) (NX10, Park Systems Corp., Suwon, Korea) equipped with a noncontact cantilever at a scanning speed of 0.5 Hz. The TGA was performed by heating up to 900° C. at 5° C./min in the atmosphere of $N_2$. Specific surface area was measured according to the Brunauer, Emmett and Teller (BET) method based on nitrogen adsorption at 77 K by using BELSORP-minill (BEL, Osaka, Japan).

Preparation of a Complex Through COF-5 Synthesis on the Surface of CNT or Graphene A complex of carbon material with the COF-5 core-shell structure was prepared by in situ synthesis of COF-5 set forth below.

Above all, CNT (15 mg) was added into a solvent mixture of mesitylene (10 mL) and 1,4-dioxane (10 mL), added with benzene-1,4-diboronic acid (BDBA) (185 mg, 1.116 mmol) and 2,3,6,7,10,11-hexahydroxytriphenylene (HHTP) (241.5 mg, 0.745 mmol). Then, the mixture was treated with ultrasonic wave of 20 kHz at 160 W for 2 hours using the chip-type sonicator (Digital Sonifier® Branson). A thus-produced precipitate was repeatedly centrifuged (20,000 g, 0.5 h), was collected to wash with acetone (500 mL or more), and was then dried in a vacuum oven at 40° C.

A complex of graphene and COF-5 were prepared in the same process.

Both complexes of graphene and CNT exhibited 55% to 65% yields on the basis of the starting materials.

Experimental Example 1: Morphology of a Complex Prepared by COF-5 Synthesis on the Surface of CNT or Graphene Aromatic molecules, such as benzene, pyrene, anthracene, triphenylene, and porphyrin derivatives, have been used as building blocks for the COFs. Such molecules have been used as superior CNT- and graphene-dispersants due to their strong π-π interactions. The CNT adsorbing the aromatic molecules is solvated according to the ultrasonic treatment process, and a well-dispersed CNT solution can be obtained.

Figure 2:
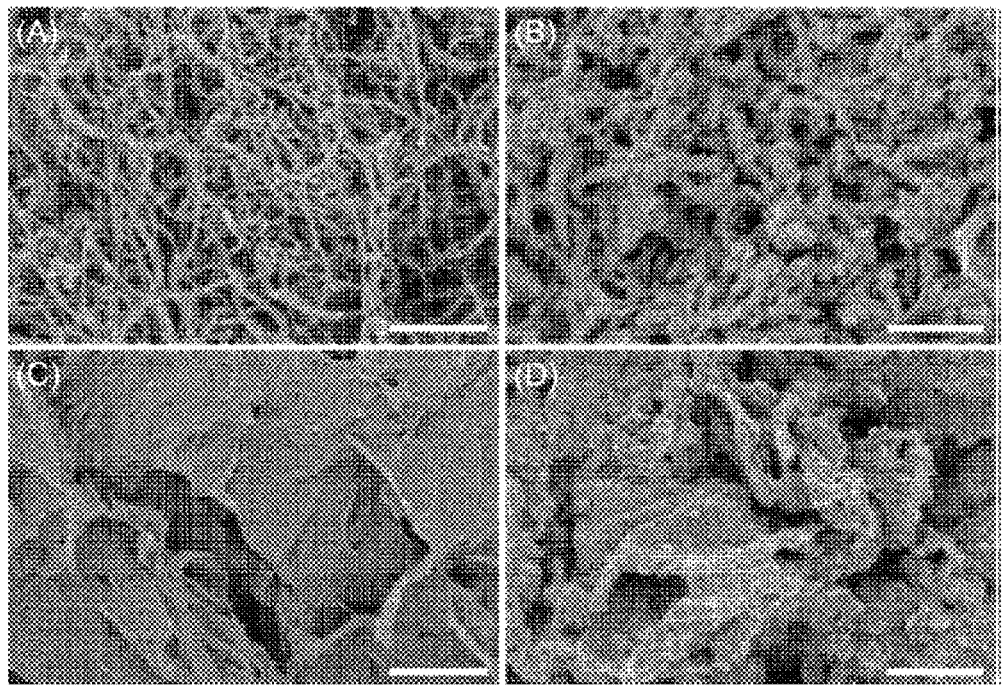
FIG. 2 is SEM (scanning electron microscope) images of (A) CNT, (B) CNT@COF-5, (C) graphene, and (D) graphene@COF-5, wherein the scale bar is 500 nm.
Figure 3:
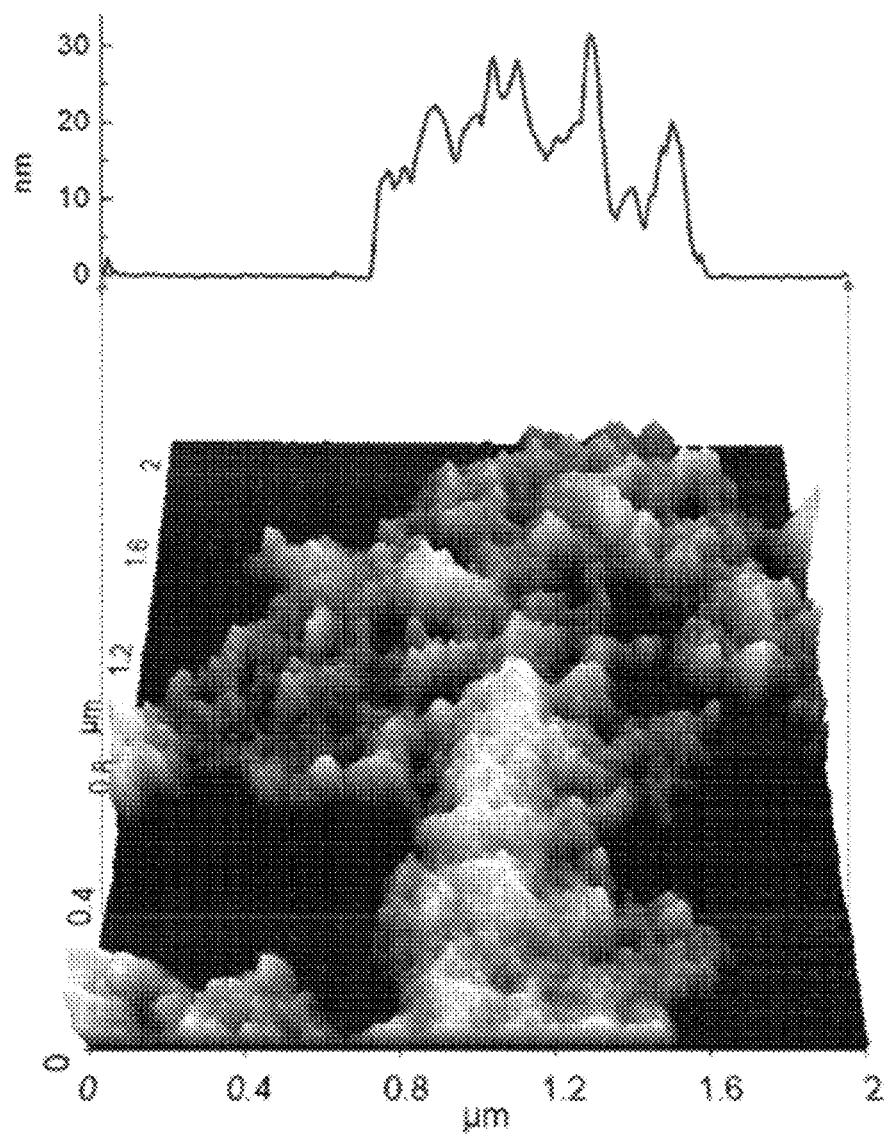
FIG. 3 is a 3D AFM image of graphene@COF-5, and a height profile extracted therefrom.

As shown in FIG. 2, the composite of CNT and COF-5 (CNT@COF-5) showed thicker diameter than those of the pristine CNTs while maintaining its shapes, suggesting the well-controlled decoration of COF-5 on CNT surfaces. As shown in FIG. 3, the graphene flakes decorated by the COF-5 (graphene@COF-5) also exhibited shapes with thicker 2D plates of 10 nm or thicker.

Figure 4:
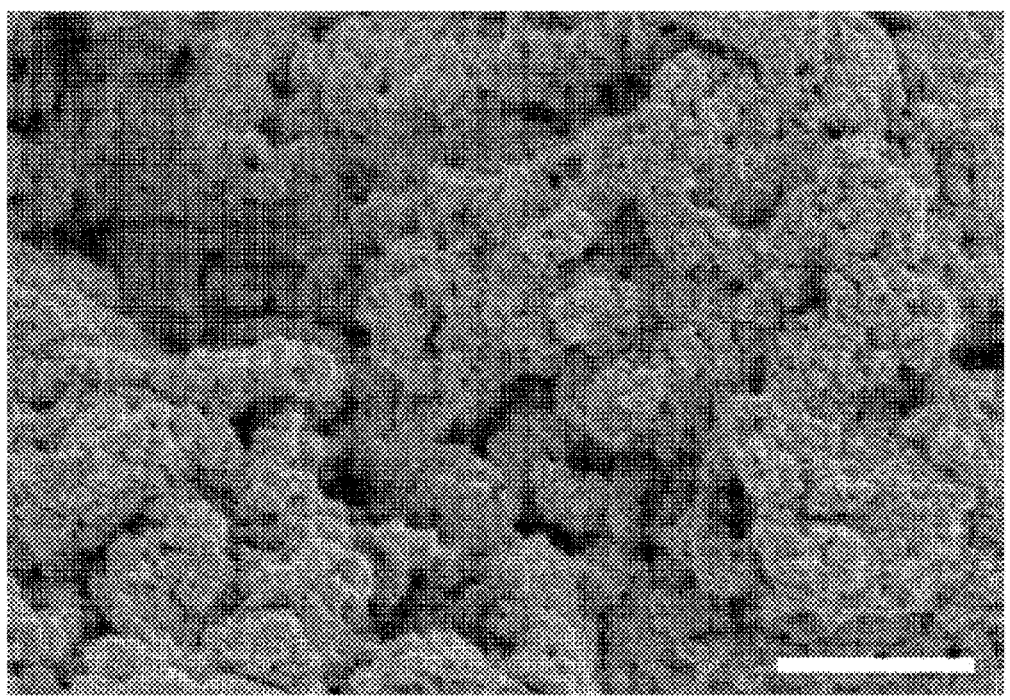
FIG. 4 is an SEM image of COF-5 synthesized without a supporting material, wherein the scale bar is 500 nm.
Figure 5:
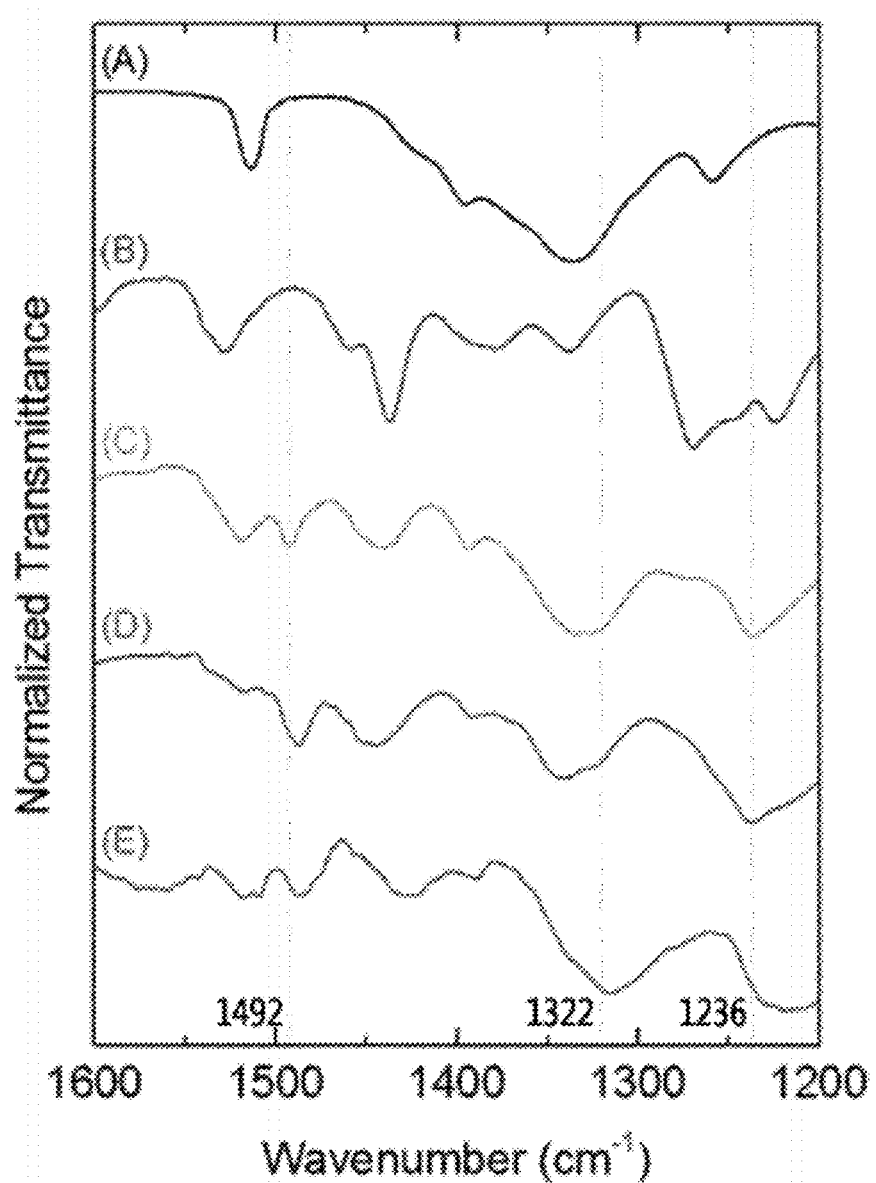
FIG. 5 is Fourier transform infrared (FT-IR) spectra of (A) BDBA, (B) HHTP, (C) COF-5, (D) CNT@COF-5, and (E) graphene @COF-5.
Figure 6:
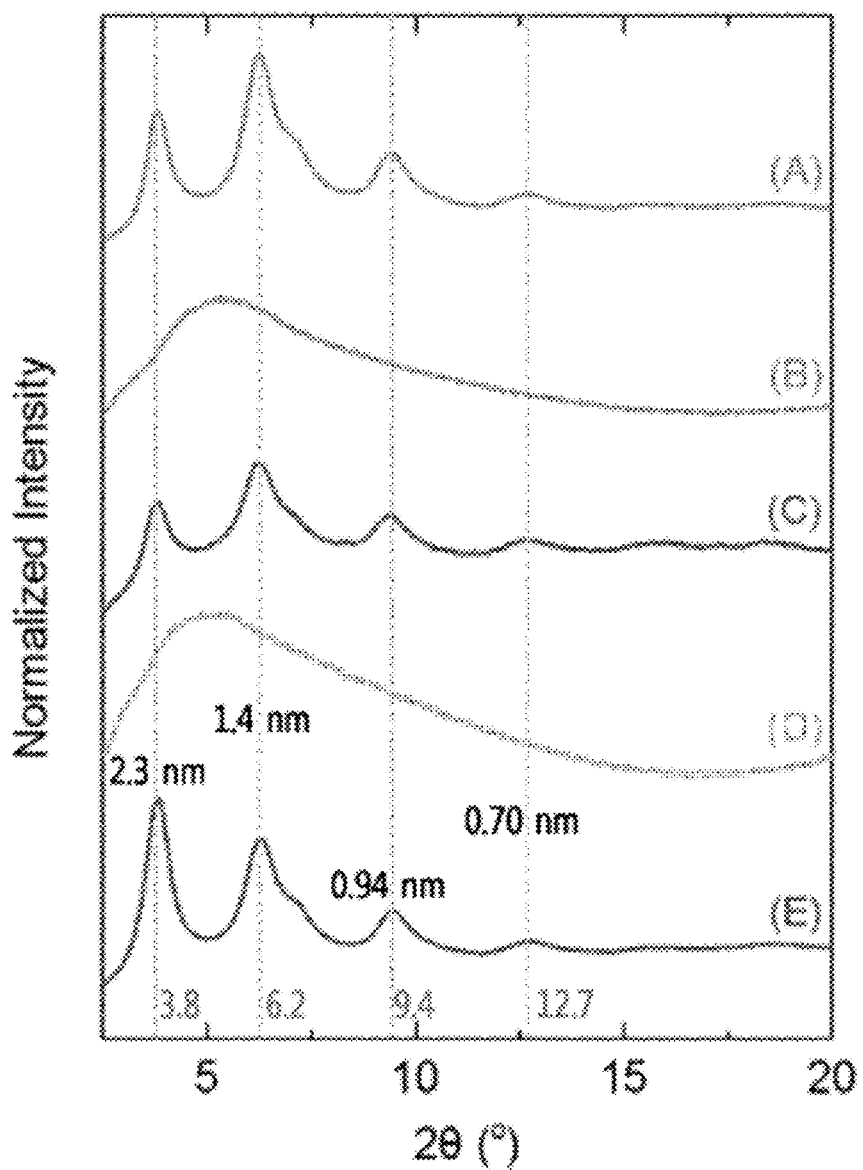
FIG. 6 is X-ray diffraction (XRD) patterns of (A) COF-5, (B) CNT, (C) CNT@COF-5, (D) graphene, and (E) graphene@COF-5.

The decorated COF-5 materials were found to exhibit morphologies similar to the COF-5 material synthesized without supporting materials (FIG. 4). Fourier transform infrared (FT-IR) spectra also indicated the formation of COF-5 as shown in FIG. 5; the newly appeared peaks at 1325 and 1236 $cm^{-1}$ are attributed to the B-O and C-O vibrations, respectively, produced by covalent bonds between boronic acids of benzene-1,4-diboronic acid (BDBA) and hydroxy groups of 2,3,6,7,10,11-hexahydroxytriphenylene (HHTP). Furthermore, the X-ray diffraction (XRD) patterns of the complexes showed patterns similar to the corresponding COF-5 (FIG. 6) and all the obtained results strongly suggested the formation of the COF-5 nanocomposites.

Experimental Example 2: $CO_2$ Adsorption Capacity

The $CO_2$ adsorption experiment was conducted with TGA Q500 (TA Instruments, New Castle, USA) according to previously reported methods (E. P. Dillon et al., ACS Nano, 2008, 2, 156-164; E. A. Roth et al., Energy Fuels, 2013, 27, 4129-4136; W. Wang et al., Appl. Energy, 2014, 113, 334-341). $N_2$ and $CO_2$ were used as gases for purge and furnace at the flow rates of 40 mL/min and 60 mL/min, respectively. The experiments were conducted after confirming no change in the weight of $N_2$ followed by purging the sample of moisture and gas with $N_2$ for 4 hours. The temperature of the furnace was raised to 70° C. at 20° C./min, and the furnace was changed to $CO_2$. After an isothermal process at each temperature (70, 55, 40, and 25° C.) for 3 hours, the furnace gas was changed from $CO_2$ to $N_2$ during heating from 25° C. to 70° C.

Figure 7A:
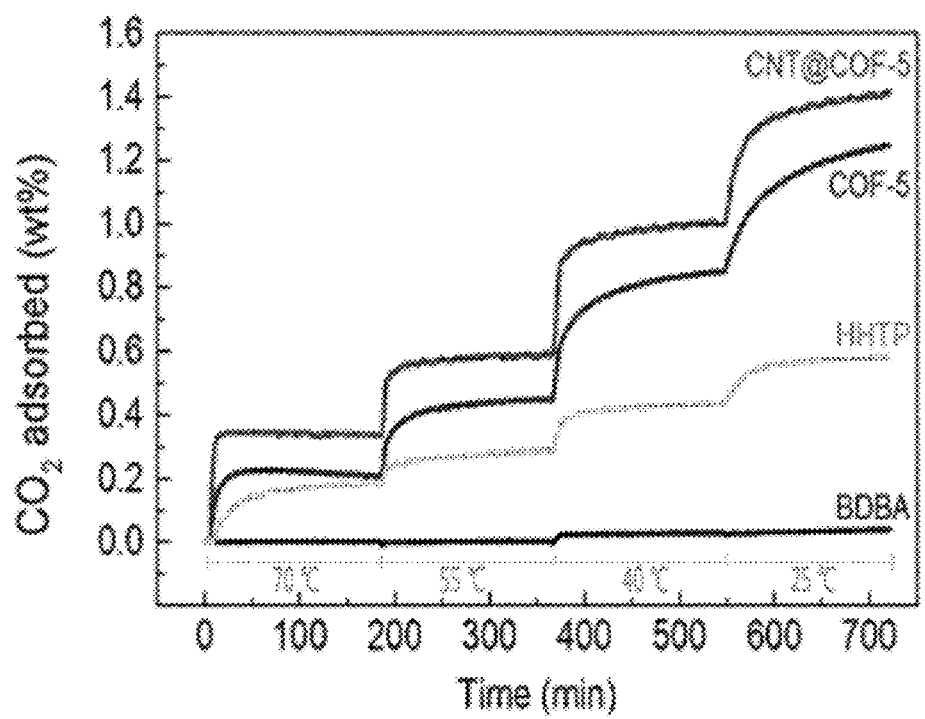
FIG. 7 is thermogravimetric analysis (TGA) graphs showing the change of mass caused by $CO_2$ adsorption of (A and B) BDBA, (A and B) HHTP, (A and B) COF-5, (A) CNT@COF-5, and (B) graphene@COF-5.
Figure 7B:
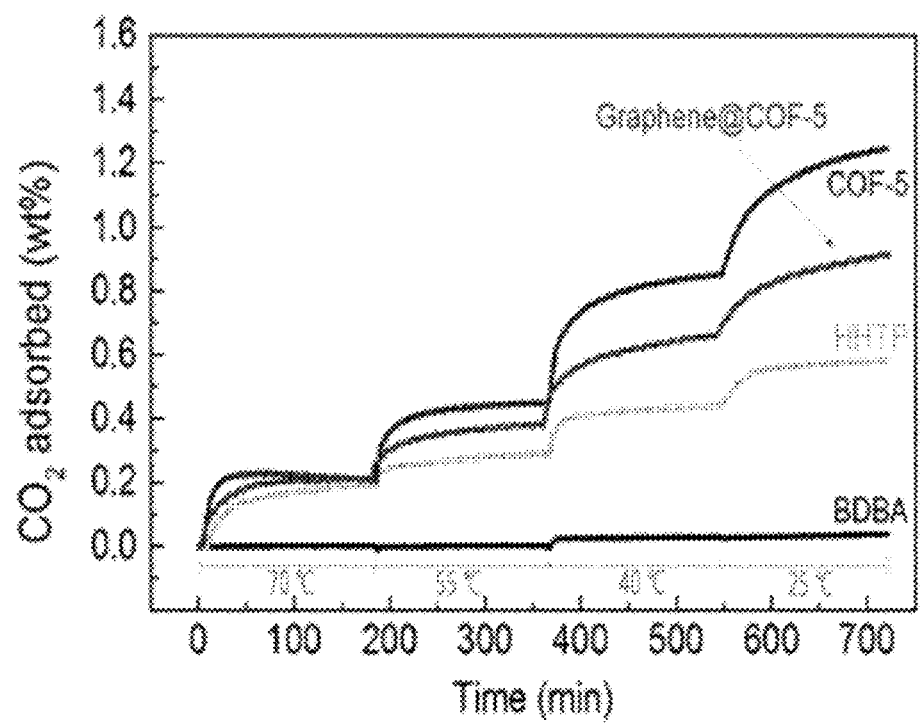
Figure 8A:
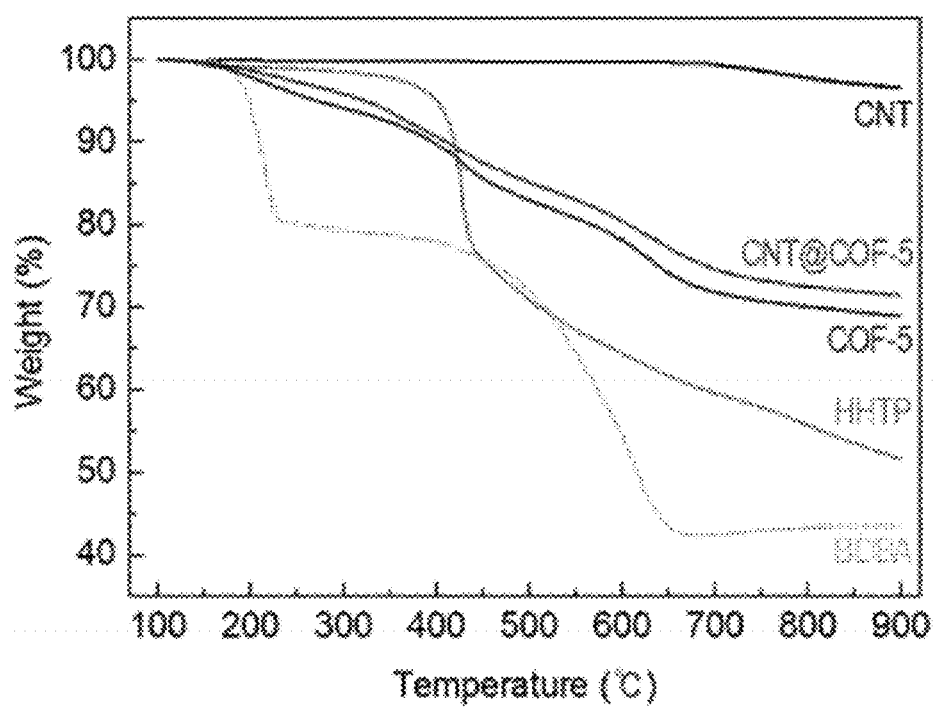
FIG. 8 is TGA graphs of (A) CNT, (A) CNT@COF-5, (B) graphene, and (B) graphene@COF-5, along with those of COF-5, HHTP, and BDBA for comparison.
Figure 8B:
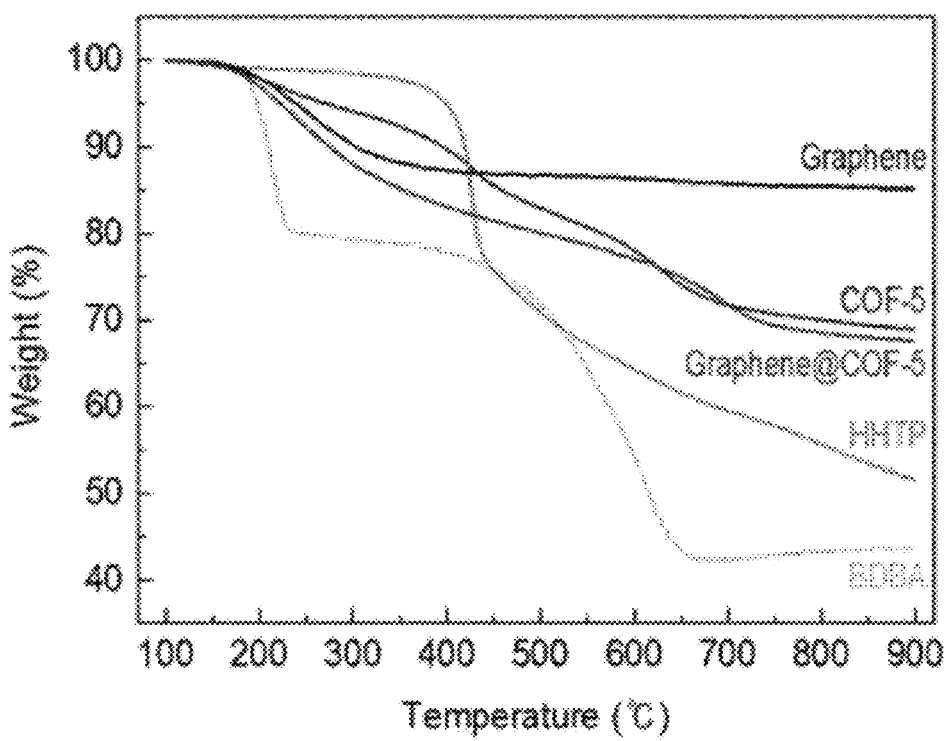

As shown in FIG. 7, the pristine COF-5 showed higher $CO_2$ adsorption capacity (1.25 wt %) than that of the CNTs (0.24 wt %) and graphene (0.48 wt %) as well as COF-5 reactants such as BDBA (0.04 wt %) and HHTP (0.58 wt %), under the same conditions, which indicates the formation of porous nanostructures within COF-5. Interestingly, it has been found that CNT@COF-5 (1.42 wt %) exhibits improved $CO_2$ adsorption capacity than COF-5 (1.25 wt %). Since the weight ratio of CNT in the CNT@COF-5 is negligible (FIG. 8), this improvement in $CO_2$ adsorption capacity was thought to occur in COF-5, which gives rise to changes in the nanostructure and surface behavior of the composite.

The zeolitic imidazolate framework-8 (ZIF-8), one of the metal organic structures (MOFs), using graphene quantum dots (GQDs) as the core material reportedly showed improved water vapor adsorption capacity compared to the pristine ZIF-8, which was explained by the change in hydrophilicity of the ZIF-8 surface (B. P. Biswal et al., *Nanoscale*, 2013, 5, 10556-10561). However, covalently-bonded boronate esters in the COF-5 are sufficiently rigid than the flexible coordinate bond of 2-methylimidazole in the ZIF-8, therefore, it is hard to obtain such the effect even with the CNT core.

The improved $CO_2$ adsorption capacity of CNT@COF-5 may be demonstrated by the specific surface areas in Table 2 below.

TABLE 2

|  | COF-5 | CNT@COF-5 | Graphene@COF-5 |
|---|---|---|---|
| Surface area ($m^2g^{-1}$) | 8.17 | 57.6 | 9.83 |
| Pore volume ($cm^2g^{-1}$) | 0.0223 | 0.220 | 0.0773 |
| Pore size (nm) | 10.9 | 14.8 | 31.5 |
| $CO_2$ uptakes (wt %) | 1.25 | 1.42 | 0.92 |

Table 2 above demonstrates that the highest specific surface area and total pore volume, which are 7 and 10 times higher than those of the pristine COF-5, respectively, are observed with CNT@COF-5⊠ This effect appears to be due to the fact that COF-5 of 2D crystal structure on a high-curvature CNT surface is difficult to form large microcrystalline, resulting in a small microcrystalline aggregate.

The invention claimed is:

1. A complex comprising a covalent organic framework (COF) synthesized on the surface of a carbon structure, wherein the carbon structure is a carbon nanotube.

2. The complex of claim 1, wherein the covalent organic framework is synthesized on the surface of the carbon structure by a sonochemical reaction.

3. The complex of claim 1, wherein the specific surface area or pore volume of the covalent organic framework synthesized on the surface of the carbon structure is larger than the specific surface area or pore volume of the covalent organic framework prepared without the carbon structure in the same synthesis conditions.

4. The complex of claim 1, wherein reactants used for synthesizing the covalent organic framework are aromatic compounds capable of π-π stacking.

5. The complex of claim 1, wherein the covalent organic framework is COF-1, COF-102, COF-103, PPy-COF, COF-102-$C_{12}$, COF-102-allyl, COF-5, COF-105, COF-108, COF-6, COF-8, COF-10, COF-11 Å, COF-14 Å, COF-16 Å, COF-18 Å, TP-COF, Pc-PBBA COF, NiPc-PBBA COF, 2D-NiPc-BTDA COF, NiPc COF, BTP-COF, HHTP-DPB COF, x % $N_3$-COF-5(x=5, 25, 50, 75, or 100), 100% $N_3$-NiPc-COF, COF-66, ZnPc-Py COF, ZnPc-DPB COF, ZnPc-NDI COF, ZnPc-PPE COF, CTC-COF, $H_2$P-COF, ZnP-COF, CuP-COF, COF-202, CTF-1, CTF-2, COF-300, COF-LZU1, COF-366, COF-42, COF-43, COF-320, COF-102-Li, COF-103-Li, COF-102-Na, COF-103-Na, COF-301-$PdCl_2$, COF-103-Eth-trans, COF-102-Ant, or a combination thereof.

6. A method for preparing the complex of claim 1, comprising adding the carbon structure and reactants used for synthesizing covalent organic framework to a solvent, followed by ultrasonic treatment (Step 1).

7. The method of claim 6, wherein the reactants used for synthesizing the covalent organic framework form the covalent organic framework on the surface of the carbon structure through a sonochemical reaction by the ultrasonic treatment in Step 1.

8. The method of claim 6, wherein the carbon structure has a concentration in the range of 0.2 mg/mL to 2 mg/mL in the solvent.

9. The method of claim 6, wherein the reactants used for synthesizing the covalent organic framework are aromatic compounds capable of π-π stacking.

10. The method of claim 9, wherein the reactants used for synthesizing the covalent organic framework are benzene-1,4-diboronic acid (BDBA), 2,3,6,7,10,11-hexahydroxytriphenylene (HHTP), or a combination thereof.

11. The method of claim 6, wherein the reactants used for synthesizing the covalent organic framework have a concentration in the range of 10 mg/mL to 60 mg/mL in the solvent.

12. The method of claim 6, wherein the solvent is mesitylene, 1,4-dioxane, or a mixture thereof.

13. The method of claim 6, wherein ultrasonic wave of the ultrasonic treatment is in the range of 20 kHz to 1,000 kHz.

14. The method of claim 6, wherein the ultrasonic treatment is conducted at an output power of 50 W to 500 W for 30 minutes to 6 hours.

15. A composition of adsorbing, storing, separating, or concentrating gases comprising the complex of claim 1.

16. The composition of claim 15, wherein the complex is used as a catalyst.

17. A gas sensor comprising the complex of claim 1.

18. The gas sensor of claim 17, wherein the gas sensor detects a gas selected from the group consisting of $CO_2$, Ar, Ne, He, $CF_4$, $H_2$, $N_2$, $O_2$, and $C_nH_{2n+2}$ (wherein n is an integer of 1 to 4).

19. The complex of claim 1, wherein the carbon nanotube comprises multi-walled carbon nanotubes.

20. A method for preparing a complex comprising a covalent organic framework (COF) synthesized on the surface of a carbon structure, the method comprising:
   adding the carbon structure and reactants used for synthesizing the covalent organic framework to a solvent to form a mixture, wherein:
      the carbon structure has a concentration in the range of 0.2 mg/mL to 2 mg/mL in the solvent; and
      the reactants used for synthesizing the covalent organic framework have a concentration in the range of 10 mg/mL to 60 mg/mL in the solvent; and
   ultrasonically treating the mixture.

* * * * *